US00PP08153P

United States Patent [19]

Austin

[11] Patent Number: Plant 8,153

[45] Date of Patent: Feb. 23, 1993

[54] ROSE PLANT — 'AUSLEAP'

[75] Inventor: David C. H. Austin, Albrighton, England

[73] Assignee: David Austin Roses, Wolverhampton, England

[21] Appl. No.: 623,287

[22] Filed: Dec. 6, 1990

[51] Int. Cl.[5] ..... A01H 5/00

[52] U.S. Cl. ..... Plt./1

[58] Field of Search ..... Plt. 1, 22

*Primary Examiner*—Howard J. Locker

*Attorney, Agent, or Firm*—Ladas & Parry

[57] ABSTRACT

A new variety of rose plant of the shrub class distinctive in its character by its fully double, apricot flowers with abundant continual blooming, and the unusual blend of coloring and shaping of the flowers.

1 Drawing Sheet

BACKGROUND OF THE INVENTION

The present invention relates to a new and distinct variety of shrub roses, said new variety originating as a single seedling resulting from a definite effort to produce an improvement in this class of rose.

BRIEF SUMMARY OF THE INVENTION

Primary features of this new variety which connote a distinctive advance over existing types are the vigorous abundant and continual blooming that occurs for 5 months taken with the perfection of the fully double flowers of an old-fashioned shape, more particularly apparent in the accompanying illustration of a specimen thereof.

BRIEF DESCRIPTION OF THE DRAWING

The accompanying illustration shows typical cultivar flowers of this new cultivar in various stages of development, depicted in color as nearly true as is possible to make the same in color illustrations of this character.

DETAILED BOTANICAL DESCRIPTION

The following is a detailed description of the new variety, color terminology being in accordance with the "Methuen Handbook of Colour" published by Eyre Methuen Ltd (1963).

Variety denomination (in accordance with the UPOV Convention): Ausleap.

*Cultivar trade name.*—Sweet Juliet.

*Type.*—Hardy, bushy, outdoor, cut flowers, garden decoration.

*Class.*—Shrub.

Propagation: The variety holds its distinguishing characteristics through succeeding propagations by budding.

Asexual reproduction of the new cultivar by budding has taken place at a nursery in Albrighton, Nr. Wolverhampton, England and was derived as follows Female parent (seed parent): Graham Thomas (non-patented).

Male parent (pollen parent): Admired Mirander (non-patented).

The operation of the artificial pollination is therefore expressed by the following: Graham Thomas×Admired Mirander.

The following observations are made of specimens grown outdoors in England.

PLANT DESCRIPTION

Plant:

*Height.*—100 cm.

*Habit.*—Strong, bushy and upright.

Branches:

*Young stems.*—color: 29D8 deep green, youngest parts shaded with 11D7 browish violet. Texture: Smooth. Thorns: 1-3 per node and 9 mm long. The thorns are 11E8 garnet red fading to 9D5 greyish red with sparse red glandular hairs.

*Old stems.*—29E8 deep green. Texture: Smooth. Thorns: Occasional thorns (1 to 0 per node) which are 10C6 brownish red.

LEAVES

Stipules:

*Length.*—average 20 mm.

*Width.*—6 mm.

*Angle of wingtips to petiole.*—45°-90°.

*Color.*—Medium green 30C6.

*Margins.*—Finely toothed, red-tipped glandular hairs. Wings 29C7 apple green. Mid rib 10C6 brownish red.

*Shape.*—Wings linear or slightly convex.

Petiole:

*General description.*—Length: Variable 95-115 mm. Upperside color: 29D7 greyish green tinged with 10D7 brownish red. Groove/hairs/thorns: Along groove margins and at nodes. Groove sparsely lined with red tipped glandular hairs. Underside: Mid line 1A3 pale yellow. Hair/-thorns: 10C6 brownish red 1 or 2 per node.

Leaflets.—Number: 3, 5, 7.

*Shape.*—Oval. Cuspidate apex. Rounded base, large.

*Serration.*—Serrate.

*Texture.*—Fairly soft.

General effect of foliage: Medium dense—semi glossy.

Color:

*Young foliage.*—Upperside: 29E7 bracken green tinged with 11E8 garnet red at margins. Underside: 30D6 tinged with 11D5 greyish red, margins 11E8 garnet red.

*Adult foliage.*—Upperside: 28F6 dark green. Underside: 29E6 spinach green, margins 11E8 garnet red.

INFLORESCENCE

Number of flowers per stem: 1-5.

Peduncle:

*Length.*—Variable 20–40 mm. 1st flowers tend to have longer peduncles than later flowers on the same stem group.

*Color.*—30D7 lettuce green+shaded with 9C5 greyish red.

*Thorns/hairs.*—Medium dense red tipped glandular hairs.

Sepals:

*Upperside color.*—29C7—Apple green. Widely shaded with 10C6 brownish red.

*Outer margins.*—Red tiped glandular hairs and ensiform protrusions.

*Inner margins.*—Densely tomentose.

*Underside color.*—29C7 apple green, tomentose.

*Texture.*—Slightly ridged with sparse red tipped glandular hairs.

*Sepal length.*—Average 25 mm.

Bud

*Shape.*—Rounded with long cuspidate apex.

*Length.*—25-30 mm before bud break.

*Max width.*—Abourt 10 mm.

*Color when opening.*—11D7 brownish violet streaks fading through 6A5 light orange to 3A4 pastel yellow.

Flower:

*Shape.*—Compact flattened cup with tip slightly concave. Outer petals are curved down towards petiole.

*Diameter.*—About 60 mm when blooming.

*Color when opening.*—Upperside: Outer petals: Base 3A8 vivid yellow fading through 3A5 light yellow to 3A2yellowish white. Inner petals: Basal tip 3A8 vivid yellow fading through 4A4 light yellow to 5A3 pale yellow. Underside: Outer petals: Base 3A8 vivid yellow through 3A6 yellow to 5A3 pale orange. Inner petals: Basal tip 3A8 vivid yellow fading through 3A6 yellow to 7A3 pale red.

Color when blooming.—Upperside: Basal tip 3A6 yellow fading to 3A4 pastel yellowish white. Most of petal: Basal tip 3A6 yellow fading through 3A4 pastel yellow to 4A3 pale yellow. Underside: Basal tip 3A6 yellow fading through 3A4 to 5A2 orange white. Most of petal: Basal tip 3A6 yellow fading through 3A5 light yellow to 5A3 pale orange.

Coloring when finished blooming.—Upperside: Outer petals: Basal tip 2A6 yellow fading through 2A3 pale yellow to white. Inner petals: Basal tip 2A6 yellow fading through 3A3 pale yellow to 3A2 yellowish white. Underside: Outer petals: Basal tip 2A6 yellow fading through 2A3 pale yellow to white with very very pale pink specks. Inner petals: Base 3A6 yellow changing through 3A4 pastel yellow to 5A2 orange white.

Length of blooming season at production location: From June to October.

Fragrance: Very good, sweet-fruit like.

Lasting quality: Very good. Range in number of days bloom is on plant is 10–14 days. Range in number of days as cut flowers is 8–10 days.

Petals:

*Shape.*—Outside: Rounded top fairly bilobed, base cordate, slightly shouldered and petal cupped (i.e. not flat). Inside: Folded in half lengthways, top rounded, broad, roughly bilobed and base acute. Middle: Ovate, top broad, rounded, base acute, slightly shouldered with petal slightly cupped. Texture: Inner petals soft, silky and outer petals firms. Number: About 90. Cleaning: Good, drops its petals quickly leaving tidy looking rose.

Stamens:

*Number.*—About 70.

*Anthers.*—Golden yellow.

*Filaments.*—Yellow, irregular heights.

Pistils:

*Number*—55-60.

*Stigmas.*—Straw colored.

*Styles.*—30A2 pale green/coloring at base, 5A3 brownish red at top as style expands into stigma, hairy.

Receptacle:

*Color.*—29D8 deep green.

*Texture.*—Smooth, very slightly hairy.

*Size.*—Max. width 10 mm/height 6–8 mm.

*Shape.*—Goblet shape.

THE DEVELOPMENT

Vegetation: Vigorous.

Blooming: Abundant and continual.

Aptitude to bearing fruits: None.

Resistance to frost: Good.

Resistance to disease: Very Good.

I claim:

1. A new and distinct variety of rose plant of the shrub class, characterised as to novelty by its fully double flowers of an overall apricot coloring, with abundant and continual blooming and the unusual blend of coloring and shaping of the flower being substantially as shown and described.

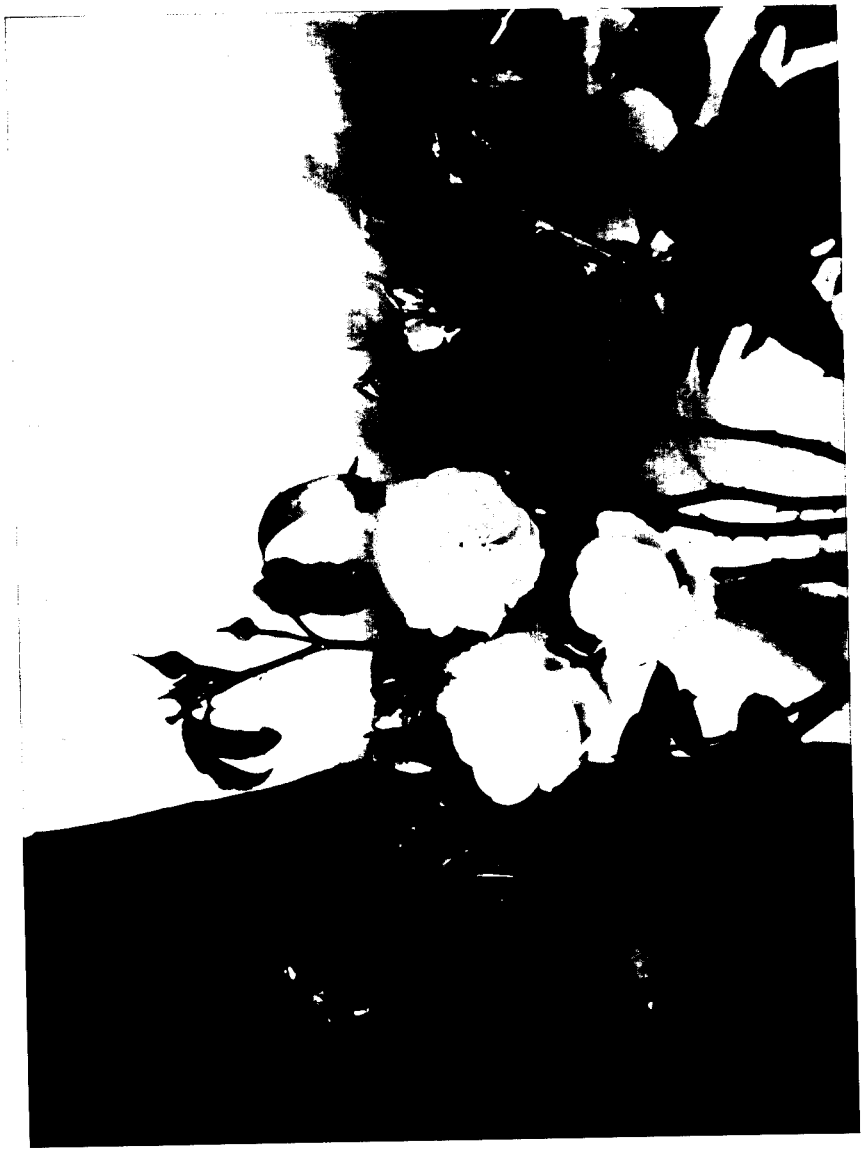

* * * * *